United States Patent [19]

Lin et al.

[11] Patent Number: 4,895,597

[45] Date of Patent: Jan. 23, 1990

[54] RECOVERY OF PRECIOUS METALS

[75] Inventors: Wilson L. Lin, Plymouth; Phillip L. Mattison, New Brighton; Michael J. Virnig, Fridley, all of Minn.

[73] Assignee: Henkel Corporation, Ambler, Pa.

[21] Appl. No.: 300,525

[22] Filed: Jan. 23, 1989

Related U.S. Application Data

[62] Division of Ser. No. 819,778, Jan. 16, 1986, Pat. No. 4,814,007.

[51] Int. Cl.$^4$ ............................................. C22B 11/04
[52] U.S. Cl. .............................. 75/118 R; 75/101 BE; 75/105; 75/106; 75/121; 210/660; 210/684; 210/685; 210/688; 210/904; 423/22; 423/24; 423/26; 423/DIG. 14
[58] Field of Search .............. 75/118 R, 101 BE, 105, 75/106, 121; 210/660, 684, 685, 688, 904; 423/22, 24, 26, DIG. 14

[56] References Cited

U.S. PATENT DOCUMENTS

| | | | |
|---|---|---|---|
| 3,473,921 | 10/1969 | Schmuckler | 75/118 R |
| 4,605,504 | 8/1986 | Van Elven et al. | 423/DIG. 14 |
| 4,774,003 | 9/1988 | Miller et al. | 423/24 |
| 4,793,852 | 12/1988 | Harris et al. | 423/26 |

OTHER PUBLICATIONS

G. Koster and G. Schmuckler, Analytica Chimica Acta, 38 (1967), pp. 179–184.

*Primary Examiner*—Robert L. Stoll
*Attorney, Agent, or Firm*—Ernest G. Szoke; Wayne C. Jaeschke; Patrick J. Span

[57] ABSTRACT

Recovery of precious metals such as gold and silver from aqueous cyanide solutions thereof, by contact with a reagent containing a guanidine functionality. The guanidine reagent extracts the precious metal from the aqueous solution which is subsequently stripped from the guanidine reagent and recovered by conventional methods. Certain novel guanidine compounds suitable for extracting gold and silver are disclosed.

14 Claims, No Drawings

RECOVERY OF PRECIOUS METALS

This application is a division of application Ser. No. 06/819,778, filed Jan. 16, 1989, U.S. Pat. No. 4,814,007, issued Mar. 21, 1989.

FIELD OF THE INVENTION

This invention relates to the recovery of precious metals such as gold and silver and in particular to the recovery of gold from aqueous cyanide solutions thereof. The recovery is achieved by contact of the aqueous cyanide solution containing the precious metals, particularly gold, with a reagent containing a guanidine functionality. The guanidine reagent extracts the gold from the aqueous solution and is subsequently stripped from the guanidine reagent and recovered by conventional methods. The invention also relates to certain novel guanidine compounds which are suitable for extracting gold from cyanide solutions.

BACKGROUND OF THE INVENTION

Gold occurs primarily as the native metal, alloyed with silver or other metals or as tellurides. It is commonly associated with the sulfides of iron, silver, arsenic, antimony and copper. Silver occurs as finely disemminated metal in rocks of hydrothermal origin as silver chloride, sulfide or tellurides and as complex sulfides with antimony and arsenic. Historical practice with ores containing native metal involve crushing, concentration of the gold or silver by gravity separation and recovery by amalgamation with mercury. Environmental concerns have resulted in abandonment of this process in most cases. Currently there are two major processes for recovery of gold and/or silver. The most widely accepted processes today involve leaching with caustic cyanide solution coupled with recovery of the metal values by concentration with zinc dust (Merrill-Crowe) or concentration of the gold and silver cyanide complexes by absorption on charcoal followed by electrowinning (carbon absorption scheme) also referred to as Carbon in Pulp (CIP). Another process recently practiced in the Soviet Union is one in which quaternary amine ion exchange resins are employed as a replacement of charcoal in the carbon absorption scheme.

In a recent publication *"Selectivity Considerations in the Amine Extraction of Gold from Alkaline Cyanide Solutions"* by M. A. Mooiman and J.D. Miller in *"Minerals and Metallurgical Processing"*, August 1984 Pages 153–157, there is described the use of primary, secondary and tertiary amines to which have been added certain Lewis base modifiers such as phosphorus oxides and phosphate esters for the extraction of gold from alkaline cyanide solutions.

The leach liquors containing the gold are achieved by leaching with cyanide solutions through either the dump or heap leaching techniques. In heap leaching, the ore is placed on specially prepared impervious pads and a leaching solution is then applied to the top of the heap and then allowed to percolate down through the heap. The solution containing the dissolved metal values eventually collects along the impervious pads and flows along it to a collection basin. From the collection basin, the solution is pumped to the recovery plant. Dump bleaching is similar to heap leaching in which old mine wastes dumps which have sufficient metal value to justify processing are leached in place. Successful dump leaching requires careful control of leach solutions to prevent ground water contamination. Heap leaching is replaced by vat leaching in areas with harsh winters, wet tropical climates or limited oxygen availability. In vat leaching the crushed ore is placed in a vat which is then flooded with leaching solution. In any of the leaching methods, a cyanide leach solution is obtained from which the metal values are recovered. While cyanide leaching is in general use today, it is relatively slow and has toxic disadvantages. Other leaching solutions are being considered in which thiourea, i.e. acido thiourea is employed, and/or thiocyanates. However, cyanide solutions appear to be the reagent of choice as a primary lixiviant for gold.

In the CIP process, coconut shell activated carbon is necessary, which is in short supply and expensive. In the Merril-Crowe process zinc dust is used to precipitate gold from the clarified cyanide solution, but the cost of this process to separate gold from leach liquors is similar to that of the CIP method.

Different amine functionalities have been considered in the past in both the liquid/liquid extraction and liquid/solid extraction of gold. For liquid/solid extraction auricyanide is too strongly bound with the quaternary amines of the resins, so that stripping is difficult and requires special treatment. In addition, no selectivity of metal cyanide complexes and leach liqors is shown. Resins with weaker basic amine functionalities cannot perform well in the pH range (10–11), the pH of the common leach liqors. For liquid/liquid extraction such as the work of Mooiman and Miller, organophosphorus modifiers, i.e. trialkylphosphates are required to increase the amine basicity in order to permit efficient extraction of the gold materials. These materials must be used in large amounts. The systems still do not reach or meet the pH criteria of leach liqors.

BRIEF SUMMARY OF THE INVENTION

It has now been discovered that certain compounds having a guanidine functionality provide a method for extraction and recovery of precious metals such as gold and silver. The guanidine functional reagents provide both a liquid/solid and a liquid/liquid system which is useful at the pH levels of the cyanide leach solutions commonly employed in processes for recovering gold.

In a liquid/liquid extraction method, the reagent must be soluble in an organic solvent which is immiscible in relation to the aqueous cyanide leach solution. Thus, the guanidine reagent is dissolved in the organic solvent, which is then brought in contact with the aqueous cyanide solution containing the desired metal values. The guanidine reagent extracts the gold and/or silver metals from the cyanide leach solution which are now found in the organic phase which is immiscible with the aqueous phase. After separation of the organic phase from the aqueous phase, the organic phase containing the desired metal values are then stripped by contact with an aqueous caustic solution which strips the metal values from the organic phase. The metal values now in a more concentrated aqueous solution are then recovered in conventional methods such as those used in the carbon absorption method through electro-winning.

In the liquid/solid extraction method, a guanidine reagent is first incorporated into a solid ion exchange carrier. Recovery of the gold from the cyanide solution is accomplished by contacting the cyanide solution with the ion exchange reagent carrier containing the guanidine functionality, at which point the metals are extracted from the aqueous cyanide solution onto the ion exchange carrier containing the guanidine reagent. The metal barren aqueous solution is then separated from the carrier containing the guanidine. The metal values are then stripped from the ion exchange carrier containing the guanidine functionality and recovered in the same manner as in the liquid/liquid extraction method.

Accordingly, the present invention is directed to a process for the recovery of precious metals such as gold or silver from an aqueous solution containing such metal values comprising (1) contacting the aqueous solution with a compound containing a functional guanidine group to extract at least a portion of the precious metal values from the aqueous solution (2) separating the resultant metal-barren solution from the guanidine compound, and (3) recovering the precious metals from the guanidine compound.

The present invention is further directed to certain novel guanidine compounds and novel ion exchange resins carrying a guanidine functionality. By guanidine functionality is meant those compounds, reagents or ion exchange resins containing the functional group:

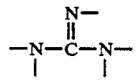

In regard to the ion exchange resins the group is bonded by chemical reaction to the resin through any one of the N atoms. The remaining bonds of the nitrogen atom are filled by hydrogen, aliphatic or aromatic hydrocarbon groups or cyclic (including heterocyclic groups containing nitrogen atoms), straight or branched chain, saturated and unsaturated, as will be discussed in more detail in the description to follow. Aspects and advantages of the present invention will be apparent to those skilled in the art upon consideration of the following detailed description thereof.

DETAILED DESCRIPTION AND PREFERRED EMBODIMENT

According to the present invention, reagents useful in the recovery of precious metal values such as gold and copper have been found which contain a guanidine functionality. These reagents possess the desirable properties necessary for successful application as an ion exchange reagent. These guanidine functional containing compounds meet a number of criteria which make them useful for this purpose. In the first instance, the guanidine compounds complex with or react with the precious metal and do so in relatively fast order, which avoids having to use large holding tanks or reaction vessels. The compounds exhibit a selectivity at designated pH ranges. The reagents exhibit satisfactory solubility in the essentially water-immiscible organic solvents used in liquid/liquid extraction systems to form the organic phases, or are capable of being rendered soluble to a sufficient extent in such organic solvent through the use of solubility modifiers. In addition, the guanidine reagent metal complexing is reversible in that the metal can be readily stripped from the organic phase. Further, compounds may be chemically reacted with ion exchange resins to provide a resin containing the guanidine functionality which is useful in liquid/solid extraction systems.

The liquid/liquid process of the invention is a liquid ion exchange process in which a water-insoluble guanidine compound is dissolved in an essentially water-immiscible liquid hydrocarbon solvent and the resulting solution is contacted with a metal-containing aqueous phase to extract a portion of the metal values into the organic phase. The phases are then separated and metal values are stripped from the organic phase by the use of an aqueous stripping medium.

A wide variety of essentially water-immiscible liquid hydrocarbon solvents can be used in the metal recovery process of the present invention. These include: aliphatic and aromatic hydrocarbons such as kerosenes, benzene, toluene, xylene and the like. A choice of the essentially water-immiscible liquid hydrocarbon solvents for particular commercial operations will depend on a number of factors, including the design of the solvent extraction plant (i.e. mixer-settler units, Podbielniak extractors, etc.), the value of the metal being recovered, and the like. The process of the present invention finds particular use in the extraction recovery of the precious metals such as gold and/or silver. The preferred solvents for use in these precious metal recovery processes of the present invention are the aliphatic and aromatic hydrocarbons having flash points of 150° F. and higher and solubilities in water of less than 0.1% by weight. The solvents are also essentially chemically inert. Representative commercially available solvents are Kermac 470B (an aliphatic kerosene available from Kerr-McGee—flash point 175° F.), Chevron ion exchange solvent (available from Standard Oil of California—flash point 195° F.), Escaid 100 and 110 (available from Exxon-Europe—flash point 180° F.), Norpar 12 (available from Exxon-USA—flash point 160° F.), Conoco-C1214 (available from Conoco—flash point 60° F.), Aromatic 150 (an aromatic kerosene available from Exxon-USA—flash point 150° F.), the various other kerosenes and petroleum fractions available from other oil companies. In the process of the present invention, the organic solvent solutions will preferably contain from about 0.02 to 20% by weight of the guanidine compound and even more preferably from about 0.1–5% by weight thereof. Additionally, volume ratios of the organic:aqueous phase vary widely since the contacting of any quantity of the guanidine solution with the metal containing aqueous phase will result in extraction of metal values into the organic phase. However, for commercial practicality, the organic:aqueous phase ratios are preferably in the range of about 50:1 to 1:50. It is desirable to maintain an effective 0 to A ratio of about 1:1 in the mixer by recycle of one of the streams. For practical purposes the extracting and stripping are normally conducted at ambient temperatures and pressures, although higher and/or lower temperatures and/or pressures are entirely operable. Most advantageously, the entire process can be carried out continuously with the stripped organic solvent solution being recycled for contacting further quantities of the precious metal-containing cyanide solutions. As indicated, in a liquid/liquid extraction process the guanidine reagent must be soluble in the organic water-immiscible solvent to the extent of about 0.02% by weight, or capable of being soluble to such extent through the use of a solubility modifier substance. Such solubility modifiers suitable for use in the present invention include longchain ($C_6$–$C_{20}$) aliphatic alcohols such as n-hexanol, n-2-ethylhexanol, isodecanol, dodecanol, tridecanol, hexadecanol and octadecanol; longchain alkyl phenols such as heptylphenol, octylphenol, nonylphenol and docecylphenol; and organo-phosphorus compounds such as tri-lower alkyl ($C_4$–$C_8$) phosphates, especially tributyl phosphate and tri(2-ethylhexyl) phosphate.

The extraction of the precious metals from their aqueous solution depends on a number of factors including, for example, the concentration of the metal ion, the particular anions present, and the pH of the aqueous solutions and the concentration of and the particular guanidine used in the organic phase. Thus, for each aqueous metal solution and reagent solution of guanidine, there will be a preferred or optimum set of extraction conditions and those skilled in the art based on the information given herein, especially in respect of the examples to follow, will be able with a limited number of trial runs to determine such preferred or optimum conditions for the specific system under consideration. This is equally true of the stripping operations. By stripping is meant that at least a portion of the metal values in the loaded organic phase are transferred to the aqueous stripping medium. The metal values are then desirably recovered from the aqueous stripping medium by conventional techniques, preferably electrolysis. The loaded organic:aqueous stripping phase ratios can also vary widely. However, the overall object of the process is to provide a metal containing stripping solution of known composition and concentration suitable for the conventional recovery techniques such as by electrolysis. Thus, normally the metal will preferably be present in higher concentrations in the aqueous stripping medium than in the starting metal-containing solution. In this regard the starting aqueous metal-containing solutions will contain 1 to 5 ppm of gold, 1 to 2 ppm of silver and 5 to 10 ppm of copper plus traces of other metals. A heap leach liquor will average 0.5 to 2 ppm gold, 0.5 to 2 ppm silver and 5 to 100 ppm copper plus other metals. The concentrations of gold in the aqueous strip solutions from which the gold will be recovered will be anywhere from about 50 to 1000 ppm. This will largely depend on the stripping solutions employed and the efficiency thereof. In the stripping step, the loaded organic:aqueous stripping medium phase ratio will preferably be in the range of about 1:1 to 20:1. The aqueous stripping solutions for use in the present invention will generally be basic stripping solutions having pH in excess of 11.0. The stripping reagent preferably employed is caustic sodium hydroxide solution having a pH above 11, generally 12 or above. After removal of the metal from the aqueous stripping solution by conventional techniques, the caustic aqueous solution was recycled.

The foregoing description has dealt with the liquid/liquid extraction systems. As earlier indicated, liquid/solid systems can be employed, in which a guanidine reagent is incorporated into an ion exchange resin by chemically bonding the guanidine functionality to the resin backbone. In this regard, the term "extracting" used herein is to be understood as including both liquid and solid means for selectively removing and otherwise separating the precious metal values. As the ion exchange resin containing the guanidine functionality will be used to treat or contact a gold-containing aqueous solution, the ion exchange resin must be one which is water-insoluble. Upon contact of the aqueous cyanide solution containing the precious metals, the precious metals are selectively absorbed by the guanidine reagent on the the ion exchange resin. The metal values are then eluted from the ion exchange resin by contact with the sodium hydroxide solution such as the stripping solution mentioned earlier above. The techniques employed in the production of water-insoluble ion exchange resins employed in the process of the present invention are well-known to those skilled in the art, and especially, to those skilled in the art of polymerizing monomers to produce polymeric compositions useful as ion exchange resins. In the present invention, the preferred ion exchange resin is a chloromethylated polystyrene, which upon chemical reaction with the appropriate compound, provides a guanidine functionality carried by the ion exchange resin. One of the preferred ion exchange resins useful in the present invention is chloromethylated polystyrene, 1.06 meq chloride/g, 2% divinylbenzene (DVB). However, the particle size of the ion exchange resin can vary widely, so long as the size range is generally fine enough to exhibit desirable loading and elution kinetics and yet large enough to (a) allow the solution to flow through the bed without binding or building up excess pressure: and (b) allow convenient screening of the resin from the aqueous solution. Preferably, about a 6–12 mesh size is employed. The loading of the water-insoluble ion exchange resins with the guanidine can vary widely. Generally, it will be determined by the bed-volume characteristics of the particular water-insoluble ion exchange resin. Typically, the flow rates through the ion exchange bed will be such as to assure effective absorption onto the water-insoluble ion exchange resins.

After the water-insoluble ion exchange resin containing the guanidine reagent has been loaded with the precious metal values, the aqueous cyanide solution is separated from the ion exchange resin and the absorbed precious metal values are eluted from the ion exchange resin. The suitable eluants as indicated are the same as the aqueous stripping solutions employed in the liquid/liquid extraction process. The most efficient and effective eluent is an aqueous solution of sodium hydroxide having a pH above 11.

As indicated, both the liquid/liquid and liquid/solid extraction processes require reagents containing a guanidine functional group which may ideally be defined as:

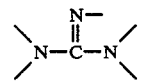

For use in the liquid/liquid extraction process there are water-insoluble guanidine compounds which are soluble in water immiscible hydrocarbon solvents, and where precious metal salts are soluble therein, to the extent of at least 0.22% by weight. For use in the extraction process, the compounds also have a pKa of greater than 12 and preferably than 13. A discussion of basic strengths of methylated guanidine and pKa values thereof can be seen in "The Basic Strength of Methylated Guanidines", S. J. Angyal and W. K. Worberton, pages 2492–2494 of J. Chem. Soc., 1951. In the liquid/solid extraction process, an ion exchange resin incorporates the guanidine functionality by chemical reaction with the guanidine compounds. Thus, the guanidine reagent suitable for use in the present extraction processes may be further illustrated by means of the idealized formula:

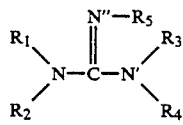

A.

wherein $R_1$ through $R_5$ is selected from the group consisting of H, an ion exchange resin backbone and aromatic and aliphatic groups having from 2-25 carbon atoms. THe guanidine compounds which are extraction reagents in the liquid/liquid system or which are chemically reacted with the ion exchange resin from the liquid/solid system are those having a pKa at 25° C. greater than 12. Aromatic groups such as phenyl, tend to decrease the basicity to a level below a pKa of 12 and accordingly not more than one of the R groups should be phenyl. The ion exchange resin may be bonded to the guanidine to any one of the nitrogen atoms such as at N'' or N or N'. Further, any two of the nitrogen atoms may form a cyclic structure with an R group, thus providing compounds of the formula:

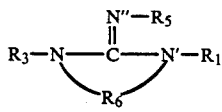

B.

where $R_6$ is an aliphatic group having from 2-25 carbon atoms. Further, any two of the nitrogen atoms such as the N, N' nitrogens, may form a cyclic structure containing additional nitrogen atoms such as in the formula:

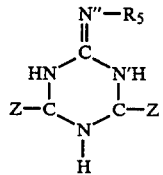

C.

where Z is $R^1$ or $NR'_2$ where R' is H, aromatic or aliphatic hydrocarbon group having 1-25 carbon atoms.

In summary, the novel guanidines of this invention are those of the formula A. above in which:
(a) no more than one R group is aromatic such as phenyl;
(b) the R groups on nitrogen N and N' may be the same or different and at least one of the groups is an aliphatic hydrocarbon group containing at least 8 carbon atoms and preferably greater than 12;
(c) no more than 3 of the R groups $R_1$ through $R_5$ may be H;
(d) the sum of the carbon atoms in the R groups $R_1$ through $R_5$ is greater than 10, more desirably at least 16 carbon atoms and preferably greater than 20 carbon atoms, but if the sum is less than 25, at least one of the R groups is branched.

To further illustrate the various objects and advantages of the present invention, the following examples are provided. It is understood that their purpose is entirely illustrative and in no way intended to limit the scope of the invention.

EXAMPLE I

In this example the synthesis of symmetrical guanidine derivatives are illustrated. Using the procedure described below, there was prepared the
(A) di-n-octyl guanidine
(B) di-2-ethylhexyl guanidine, and
(C) di-tridecyl guanidine in which the tridecyl is a mixture of isomers from the corresponding octylamine, 2-ethylhexylamine and tridecyl amine.

A solution of cyanogen bromide (5.3 g, 50 mmol) in octane (100 ml) was added to an octane solution (200 ml) with two equivalents of the amine at 0° C. After the addition, the mixture was heated to reflux at about 100° C. for 8 hours. Workup with a sodium hydroxide solution gave the crude products. The yields were 90-100%. The products were the evaluated as extractants.

EXAMPLE II

In this example there is illustrated the preparation of an unsymmetrical guanidine derivative via a cyanamide intermediate.

There was prepared N-2-ethylhexylcyanamide by adding 2-ethylhexylamine (6.5g, 50 mmol) to a solution of octane (100 ml) containing cyanogen bromide (5.3g, 50 mmol) in the presence of one equivalent of triethylamine at 0° C. The salt of triethylamine was removed by filtration. The hydrogen chloride salt of a commercially available amine, such as primary JMT $C_{12-14}$ amine of Rohm and Haas, was prepared by passing hydrogen chloride gas through an octane (200 ml) solution of 50 mmol of the amines. The two octane solutions were then mixed, and heated to reflux at about 100° C. for 8 hours. The reaction then was quenched by a solution of sodium hydroxide to give the unsymmetrical guanidine product, such as $C_{12-14}$, 2-ethylhexyl guanidine.

EXAMPLE III

In this example is illustrated the incorporation of the guanidine functionality into a water insoluble ion exchange resin.

There was synthesized N-(6-aminohexyl)-N'-butyl-guanidine via the cyanamide intermediate, N-(6-aminohexyl)-cyanamide. The intermediate was prepared by adding one equivalent of cyanogen bromide to a solution of 1.6-diaminohexane (one equivalent) in octane at 0° C. Then to this solution was added n-butylamine (five equivalents). Workup with a sodium hydroxide solution gave the desired guanidine with an amino group on the other end, which was reacted further with chloromethylated polystyrene. Chloromethylated polystyrene (1.06 meq/g, 2% DVB, 200-400 mesh) was treated with an excess amount (4 equivalents of guanidine per equivalent of chloride) of this guanidine derivative in a mixture of dimethylformamide and tetrahydrofuran, and heated to reflux for 24 hours. This modified resin then was washed with a sodium hydroxide solution, followed by water and ethanol. Finally it was dried under vacuum.

EXAMPLE IV (a). N,N'-Di-n-octylguanidine prepared in Example I was then evaluated as an extractant for gold, silver and copper from synthetic cyanide solutions containing approximately 10 ppm of gold, silver or copper in the presence of sodium cyanide (500 ppm) between pH=7 and pH=11.20. Organic solutions with 0.050 M of the extractant in 10% tridecanol (TDA) and 90% xylene were contacted with equal volumes of the cyanide solutions for 5 minutes, different pH values adjusted by either a sulfuric acid solution or sodium hydroxide solution. Subsequent analysis of the aqueous solutions for metal content indicated that the extraction percentage of gold, silver and copper was quantitative within this pH range.

(b). The other two guanidines in Example I were also evaluated as extractants for gold, silver and copper from cyanide solutions by the same procedure. Kerosene was used as a diluent, but N,N'-bis(2-ethylhexyl)-guanidine required 10% TDA as a modifier. Subsequent analysis of the aqueous phase generated the data in Table I below to obtain pH isotherms.

TABLE I

Extraction Percentage of Gold, Silver and Copper vs. pH 1. 0.050 M of N,N'—bis(trideyl)guanidine

| pH | % of Au Extraction |
| --- | --- |
| 9.85 | 100% |
| 10.90 | 100% |
| 12.20 | 90% |

| pH | % of Ag Extraction |
| --- | --- |
| 10.10 | 100% |
| 11.30 | 95% |
| 12.00 | 64% |

2. 0.010 M of N,N'—bis(tridecyl)guanidine

| pH | % of Au Extraction |
| --- | --- |
| 9.10 | 100% |
| 10.05 | 97% |
| 11.10 | 82% |
| 12.30 | 19% |

| pH | % of Ag Extraction |
| --- | --- |
| 9.55 | 93% |
| 10.70 | 46% |
| 11.65 | 9% |
| 12.20 | 0% |

| pH | % of Cu Extraction |
| --- | --- |
| 9.30 | 100% |
| 10.20 | 89% |
| 11.20 | 23% |
| 12.05 | 6% |

3. 0.050 M of N,N'—bis(2-ethylhexyl)guanidine

| pH | % of Au Extraction |
| --- | --- |
| 9.95 | 100% |
| 10.60 | 100% |
| 12.20 | 95% |

| pH | % of Ag Extraction |
| --- | --- |
| 10.35 | 100% |
| 11.70 | 76% |
| 12.30 | 35% |

| pH | % of Cu Extraction |
| --- | --- |
| 10.05 | 100% |
| 10.55 | 99% |
| 12.00 | 48% |

4. 0.010 M of N,N'—bis(2-ethylhexyl)guanidine

| pH | % of Au Extraction |
| --- | --- |
| 8.75 | 100% |
| 10.40 | 92% |
| 11.80 | 34% |
| 12.10 | 30% |

| pH | % of Ag Extraction |
| --- | --- |
| 9.50 | 56% |
| 10.00 | 34% |
| 10.75 | 21% |
| 11.85 | 4% |

TABLE I-continued

Extraction Percentage of Gold, Silver and Copper vs. pH

| pH | % of Cu Extraction |
| --- | --- |
| 9.50 | 20% |
| 10.30 | 8% |
| 11.25 | 6% |

EXAMPLE V

In order to illustrate the selectivity, a solution (15 ml) of kerosene with 0.010 M concentration of N,N'-bis-(2-ethylhexyl)guanidine was contacted by an aqueous solution (15 ml) containing approximately 8 ppm of gold, silver and copper at pH=10.30, and pH=10.90. The extraction percentage of each metal ion is shown in Table III below.

TABLE III

| pH | Au | Ag | Cu |
| --- | --- | --- | --- |
| 10.30 | 95% | 68% | 49% |
| 10.90 | 89% | 49% | 5% |

These competitive selectivity experiments show a preference of gold>silver>copper.

EXAMPLE VI

This example illustrates that gold can be recovered from the loaded organic solutions by stripping with 10% sodium hydroxide solutions. By contacting the organic solution containing the gold values with the stripping solution with an O/A of 1, the gold was quantatively recovered from the loaded organic solutions (0.050 M and 0.010 M of the extractants). Gold can be concentrated by simply changing the O/A ratio in both extraction and stripping. For stripping, gold concentration was increased from 16.9 ppm to 64 ppm (93% recovery) by stripping an organic solution (0.025 M of N,N'-bis(2-ethylhexyl)guanidine) with an O/A of 4.

The following Table IV illustrates the results of the stripping tests.

TABLE IV

| | R | O/A | Recovery Percentage |
| --- | --- | --- | --- |
| 0.050 M | tridecyl | 1 | 100% |
| 0.010 M | tridecyl | 1 | 100% |
| 0.010 M | tridecyl | 5 | 95% |
| 0.050 M | 2-ethylhexyl | 1 | 100% |
| 0.010 M | 2-ethylhexyl | 1 | 100% |
| 0.010 M | 2-ethylhexyl | 5 | 93% |
| 0.025 M | 2-ethylhexyl | 4 | 93% |

EXAMPLE VII

In this example extraction was conducted using the resin of Example III. The modified resin (1 g) was contacted overnight with an aqueous solution (20 ml) containing 10 ppm of gold in the presence of 500 ppm of cyanide. Then, the aqueous phase was filtered. Gold was quantatively extracted at pH of 10.65. In a control experiment by use of the unmodified resin, gold was not extracted at all.

EXAMPLE VIII

The gold was recovered from the loaded 1 gram of modified resin from Example VII above by stripping with 20 ml of a 10% sodium hydroxide solution. The gold was recovered in an amount of 40%.

We claim:

1. A process for the recovery of a precious metal from an aqueous alkaline cyanide solution containing said precious metal comprising:
   (1) contacting said aqueous solution containing said precious metal with an ion exchange resin having a functionality consisting essentially of guanidine functionality wherein said precious metal value is extracted from said aqueous solution, wherein said ion exchange resin containing said quanidine functionality has a pKa at 25° C. greater than 12 and has the formula:

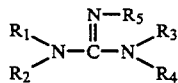

where one of the R groups $R_1$ through $R_5$ is an ion exchange resin backbone and the remaining R groups are selected from the group consisting of H and aromatic and aliphatic hydrocarbon groups having up to 25 carbon atoms;
   (2) separating said aqueous solution, now metal barren, from said ion exchange resin having said guanidine functionality; and
   (3) recovering the precious metal value from said ion exchange resin by stripping said precious metal value from said ion exchange resin by contacting said ion exchange resin with an aqueous alkaline solution.

2. A process as defined in claim 1 wherein said resin is a polystyrene resin.

3. A process as defined in claim 1 wherein said precious metal is gold or silver.

4. A process as defined in claim 1 in which said aqueous alkaline solution for stripping said precious metal value from said ion exchange resin has a pH above 11.

5. A process as defined in claim 4 wherein said aqueous alkaline stripping solution is NaOH.

6. A process as defined in claim 1 wherein the R group which is the ion exchange resin backbone is a polystyrene resin, two of the R groups are H and the remaining two R groups, which may be the same or different, are alkyl groups selected from the group consisting of n-octyl, 2-ethylhexyl, butyl, hexyl and tridecyl.

7. A process as defined in claim 6 wherein one of the two remaining R groups is butyl and the other in hexyl.

8. A precious metal cyanide complex of a guanidine compound having a pKa at 25° C. greater than 12 and having the formula:

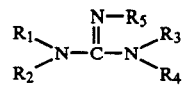

where one of the R groups $R_1$ through $R_5$ is an ion exchange resin backbone and the remaining R groups are selected from the group consisting of H and aromatic and aliphatic hydrocarbon groups having up to 25 carbon atoms.

9. A precious metal cyanide complex as defined in claim 8 wherein said precious metal is selected from the group consisting of silver and gold.

10. A precious metal cyanide complex is defined in claim 8 in which said ion exchange resin backbone is a polystyrene resin.

11. A precious metal cyanide complex as defined in claim 10 in which said precious metal is gold.

12. A precious metal cyanide complex as defined in claim 8 wherein the R group which is the ion exchange resin backbone is a polystyrene resin, two of the R groups are H and the remaining two R groups, which may be the same or different, are alkyl groups selected from the group consisting of n-octyl, 2-ethylhexyl, butyl, hexyl and tridecyl.

13. A precious metal cyanide complex as defined in claim 12 in which said precious metal is gold.

14. A precious metal cyanide complex as defined in claim 13 in which one of the two remaining R groups is butyl and the other is hexyl.

* * * * *